(12) United States Patent
Adkisson et al.

(10) Patent No.: US 10,716,546 B2
(45) Date of Patent: Jul. 21, 2020

(54) FORCEPS WITH LOCKING MECHANISM

(71) Applicant: Cook Medical Technologies LLC, Bloomington, IN (US)

(72) Inventors: Todd Adkisson, Clearwater, FL (US); Luke T. Jungles, Winston-Salem, NC (US); Kenneth C. Kennedy, II, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 263 days.

(21) Appl. No.: 15/260,676

(22) Filed: Sep. 9, 2016

(65) Prior Publication Data

US 2017/0071585 A1 Mar. 16, 2017

Related U.S. Application Data

(60) Provisional application No. 62/218,782, filed on Sep. 15, 2015.

(51) Int. Cl.
*A61B 10/06* (2006.01)
*A61B 17/29* (2006.01)
*A61B 10/04* (2006.01)

(52) U.S. Cl.
CPC .............. *A61B 10/06* (2013.01); *A61B 10/04* (2013.01); *A61B 17/29* (2013.01);
(Continued)

(58) Field of Classification Search
CPC . A61B 10/06; A61B 17/29; A61B 2017/2936; A61B 2017/2939
See application file for complete search history.

(56) References Cited

U.S. PATENT DOCUMENTS

| 5,478,350 A | 12/1995 | Kratsch et al. |
| 5,490,819 A * | 2/1996 | Nicholas .................. A61B 1/32 |
| | | 600/201 |

(Continued)

FOREIGN PATENT DOCUMENTS

| JP | 58-010716 U1 | 7/1956 |
| JP | 2014-505520 A | 3/2014 |

(Continued)

OTHER PUBLICATIONS

International Search Report and Written Opinion for International PCT No. PCT/US2016/050878, dated Dec. 5, 2016, pp. 1-14.

(Continued)

*Primary Examiner* — Daniel L Cerioni
*Assistant Examiner* — Raymond P Dulman
(74) *Attorney, Agent, or Firm* — Brinks Gilson & Lione

(57) ABSTRACT

A forceps is provided that includes a housing defining an internal passageway and a longitudinal axis, first and second jaws slidably and pivotably connected to the housing, a first connection member having a first end pivotably attached to the first jaw, a second connection member having a first end pivotably attached to the second jaw; and a driver pivotably connected to the other ends of the first connection member and the second connection member, wherein the jaws have an open configuration and a closed configuration, wherein longitudinal movement of the driver in a first direction rotates the first and second jaws relative to the housing from the open configuration towards the closed configuration, wherein longitudinal movement of the driver in the first direction also moves the first and second jaws longitudinally along the longitudinal axis of the housing from the open configuration towards the closed configuration.

8 Claims, 13 Drawing Sheets

(52) U.S. Cl.
CPC ............... *A61B 2017/2936* (2013.01); *A61B 2017/2939* (2013.01); *A61B 2017/2941* (2013.01); *A61B 2017/2946* (2013.01)

(56) References Cited

U.S. PATENT DOCUMENTS

| | | | | |
|---|---|---|---|---|
| 5,849,022 | A * | 12/1998 | Sakashita | A61B 17/29 606/174 |
| 5,968,074 | A | 10/1999 | Prestel | |
| 6,083,150 | A * | 7/2000 | Aznoian | A61B 10/06 600/564 |
| 2006/0258954 | A1 | 11/2006 | Timberlake et al. | |
| 2009/0259248 | A1 * | 10/2009 | Ganter | A61B 17/29 606/205 |
| 2011/0301637 | A1 * | 12/2011 | Kerr | A61B 17/29 606/206 |
| 2011/0319888 | A1 * | 12/2011 | Mueller | A61B 18/1445 606/41 |
| 2012/0165863 | A1 * | 6/2012 | McLawhorn | A61B 17/08 606/207 |
| 2012/0303025 | A1 | 11/2012 | Garrison | |
| 2013/0138102 | A1 * | 5/2013 | Twomey | A61B 18/1445 606/45 |
| 2013/0218199 | A1 * | 8/2013 | Kerr | A61B 17/29 606/206 |
| 2014/0236178 | A1 * | 8/2014 | Hyodo | A61B 17/29 606/130 |
| 2016/0345993 | A1 * | 12/2016 | Fry | A61B 17/29 |

FOREIGN PATENT DOCUMENTS

| | | |
|---|---|---|
| WO | WO 96/02193 A1 | 2/1996 |
| WO | WO98/57585 A1 | 12/1998 |
| WO | WO01/28427 A1 | 4/2001 |
| WO | WO2010/104755 A1 | 9/2010 |

OTHER PUBLICATIONS

Japanese Office Action dated Mar. 26, 2019 in Japanese Application No. 2018-513583.

* cited by examiner

FORCEPS WITH LOCKING MECHANISM

CROSS-REFERENCE TO RELATED APPLICATIONS

The present patent document claims the benefit of the filing date under 35 U.S.C. § 119(e) of Provisional U.S. Patent Application Ser. No. 62/218,782 filed Sep. 15, 2015, which is hereby incorporated by reference.

TECHNICAL FIELD

This invention relates to a medical device and, in particular to lockable forceps for use in various medical procedures.

BACKGROUND

Forceps are common medical devices used in a variety of procedures to grasp or engage bodily structures or other items. For example, forceps may be used to grasp tissue for hemostasis, marking, ligating, and sealing perforations. Forceps are also commonly used to obtain tissue samples during a biopsy procedure. In a biopsy, the forceps are closed around and excise a piece of tissue. The tissue and forceps are then removed from the patient for further testing.

Traditional forceps generally have two or more opposing jaws that can be opened and closed by an operator. The forceps are traditionally inserted into a patient's body lumen with the jaws in a closed position. Once the forceps are positioned near the tissue to be engaged, the jaws are opened. The jaws are then closed around the tissue, thus effectively grasping it. If a biopsy sample is desired, the forceps are then retracted and the tissue sample is torn from the surrounding tissue.

One of the problems associated with traditional forceps is the low grasping force of the jaws. While traditional forceps have a large initial closing force, the closing force continuously declines as the closure cycle progresses. Thus, once the jaws reach the closed position, the force required to reopen the closed jaws is relatively low. Therefore, while a large amount of tissue is initially grasped, the jaws have a difficult time maintaining their grip on the tissue, which may undesirably result in the tissue being released from the jaws. The low grasping force is especially concerning during a biopsy, as the forceps, in addition to grasping the tissue, must also remove the tissue, such as by tearing or cutting it. Thus, using traditional forceps includes a risk of obtaining an inadequate amount of tissue for a proper biopsy sample. Therefore, it is desirable to improve on traditional forceps by increasing the grasping force and maintaining that force throughout the closure cycle.

Additionally, forceps and similar devices are commonly used in a variety of applications outside of the medical field. In these various applications, there exists a similar desire for forceps that strongly and effectively grasp materials.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a forceps. The forceps comprises a housing defining an internal passageway and a longitudinal axis extending between proximal and distal ends of the housing, a first jaw slidably and pivotably connected to the housing, and a second jaw slidably and pivotably connected to the housing. The forceps also comprises a first connection member having a first end pivotably attached to the first jaw, a second connection member having a first end pivotably attached to the second jaw, and a driver pivotably connected to a second end of the first connection member and a second end of the second connection member. Additionally, the first and second jaws further comprise an open configuration and a closed configuration, wherein longitudinal movement of the driver in a first direction rotates the first and second jaws relative to the housing from the open configuration towards the closed configuration, wherein longitudinal movement of the driver in the first direction also moves the first and second jaws longitudinally along the longitudinal axis of the housing from the open configuration towards the closed configuration.

The forceps may also include the first connection member comprising a first link and the second connection member comprising a second link. The forceps may also include longitudinal movement of the driver in a second direction moves the first and second jaws longitudinally along the longitudinal axis of the housing from the closed configuration towards the open configuration, wherein movement of the driver in the second direction also rotates the first and second jaws relative to the housing from the closed configuration towards the open configuration. Additionally, during at least a portion of the movement of the first and second jaws from the open configuration to the closed configuration, at least one of the first and second connection members may contact the housing to urge the first and second jaws towards the closed configuration. Additionally, in the closed configuration at least a portion of at least one of the first and second links may be wedged against the housing. The forceps may further comprise a connecting pin that slidably and pivotably connects the first and second jaws to the housing. Also, the first jaw may further comprise a first opening comprising a first substantially cylindrical portion and a first substantially elongated portion, and the second jaw may further comprise a second opening comprising a second substantially cylindrical portion and a second substantially elongated portion, wherein the first and second jaws are slidable with respect to a connecting pin along the first and second substantially elongated portions of the first and second openings and pivotable within the first and second substantially cylindrical portions of the first and second openings.

In another aspect, a forceps is provided. The forceps comprises a housing defining an internal passageway and a longitudinal axis extending between proximal and distal ends of the housing, a first jaw slidably and pivotably connected to the housing, and a second jaw slidably and pivotably connected to the housing. The forceps also comprises a first connection member having a first end pivotably attached to the first jaw, a second connection member having a first end pivotably attached to the second jaw, and a driver pivotably connected to a second end of the first connection member and a second end of the second connection member. Additionally, the first and second jaws further comprise an open configuration and a closed configuration, wherein longitudinal movement of the driver in a first direction rotates the first and second jaws relative to the housing from the open configuration towards the closed configuration. Further, during at least a portion of the movement of the first and second jaws from the open configuration to the closed configuration, at least one of the first and second connection members contacts the housing to urge the first and second jaws towards the closed configuration.

In yet another aspect, a method of engaging tissue is provided. The method comprises providing a forceps comprising a housing defining an internal passageway and a longitudinal axis extending between proximal and distal ends of the housing, a first jaw slidably and pivotably connected to a distal portion of the housing, a second jaw slidably and pivotably connected to the distal portion of the housing, a first connection member pivotably attached to a first end of the first jaw, a second connection member pivotably attached to a first end of the second jaw, and a driver pivotably connected to a second end of the first connection member and a second end of the second connection member. The method also comprises advancing the forceps in a closed configuration through a body lumen until the forceps are near a target tissue site and moving the driver in a distal direction relative to the housing to move the first and second jaws to an open configuration.

Additionally, the method comprises positioning the first and second jaws adjacent to the target tissue site and securing a tissue sample within the first and second jaws by moving the driver in a proximal direction relative to the housing to rotate the first and second jaws relative to the housing from the open configuration towards the closed configuration, wherein movement of the driver in a proximal direction also moves the first and second jaws longitudinally in a proximal direction along the longitudinal axis of the housing. The method may further comprise tearing or excising the tissue sample from the target tissue site by proximally retracting the forceps while maintaining the first and second jaws in the closed configuration and withdrawing the forceps and the tissue sample from the body lumen.

DETAILED DESCRIPTION OF THE EMBODIMENTS

Figure 1:
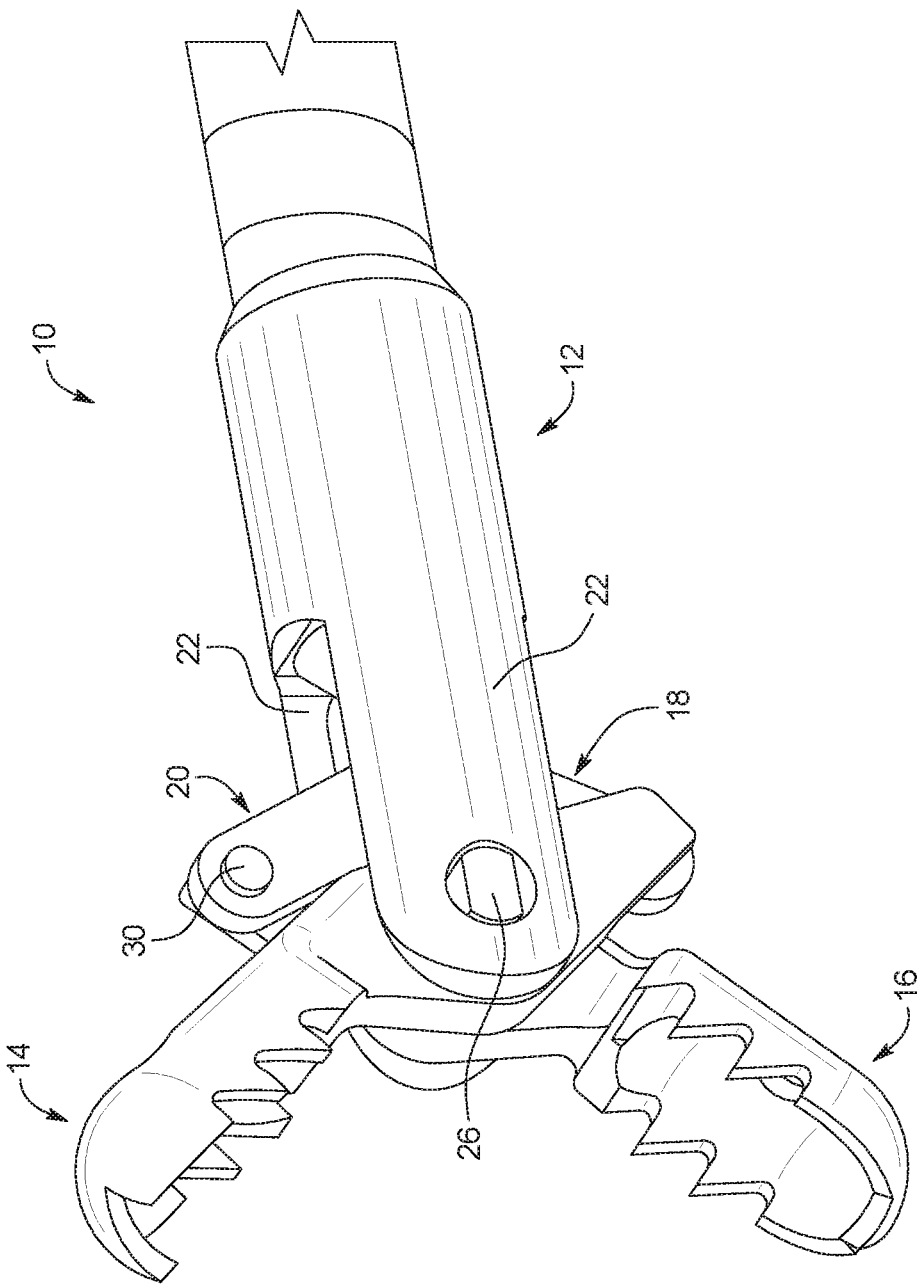
FIG. 1 is an orthographic view of a forceps design in an open configuration.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the forceps to a patient. Hence the term "distal" means the portion of the forceps that is farthest from the physician and the term "proximal" means the portion of the forceps that is nearest to the physician.

Figure 2:
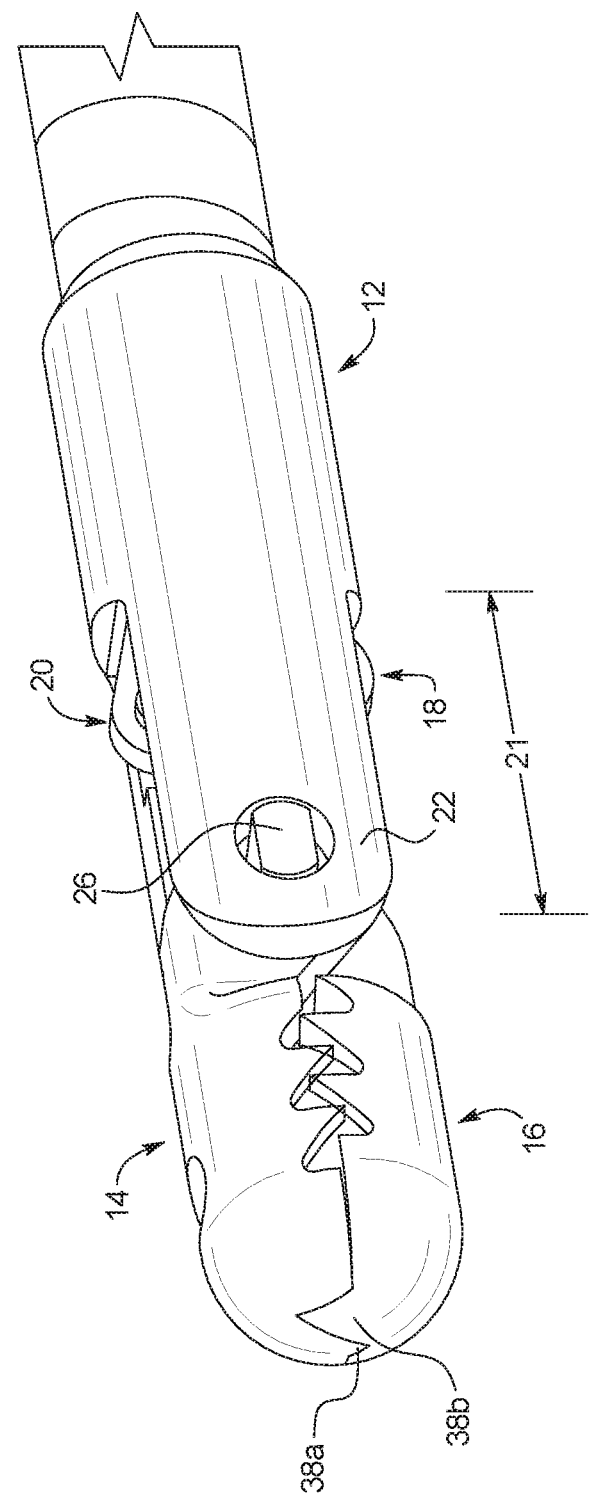
FIG. 2 is an orthographic view of a forceps design in a closed configuration.

FIGS. 1 and 2 show a forceps 10. FIG. 1 shows the forceps 10 in an open configuration and FIG. 2 shows the forceps 10 in a closed, or locked, configuration. The forceps 10 may include a housing 12, a first jaw 14, and a second jaw 16. The forceps 10 may further include a first connection member 18 and a second connection member 20. In this embodiment the first and second connection members 18, 20 are links; however, the first and second connection members 18, 20 may include other designs, including using several links placed in series to create linkages with various kinematic advantages. Each link 18, 20 may have cutout portions 17, 19, or scallops, along the sides of the links 18, 20. A distal portion 21 of the housing 12 may include a forked portion 22. A connecting pin 26 may be fixedly secured to the forked portion 22. The first jaw 14 may include a first opening 24 and the second jaw 16 may include a second opening 25 (concentric with the first opening 24 when viewed from the side angle in FIG. 3) for insertion of the connecting pin 26, thus allowing the first and second jaws 14, 16 to be slidably and pivotably connected to the forked portion 22 of the housing 12. Alternatively, two separate connecting pins may be used, one for each jaw 14, 16. The first jaw 14 may be pivotably connected to one end of the first link 18 with a first pin 28 (not shown). The other end of the first link 18 may be pivotably connected to a driver 40 (shown in FIG. 3). The second jaw 16 may be pivotably connected to one end of the second link 20 with a second pin 30 similar to the connection described above for the first pin 28. The other end of the second link 20 may be pivotably connected to the driver 40.

Figure 3:
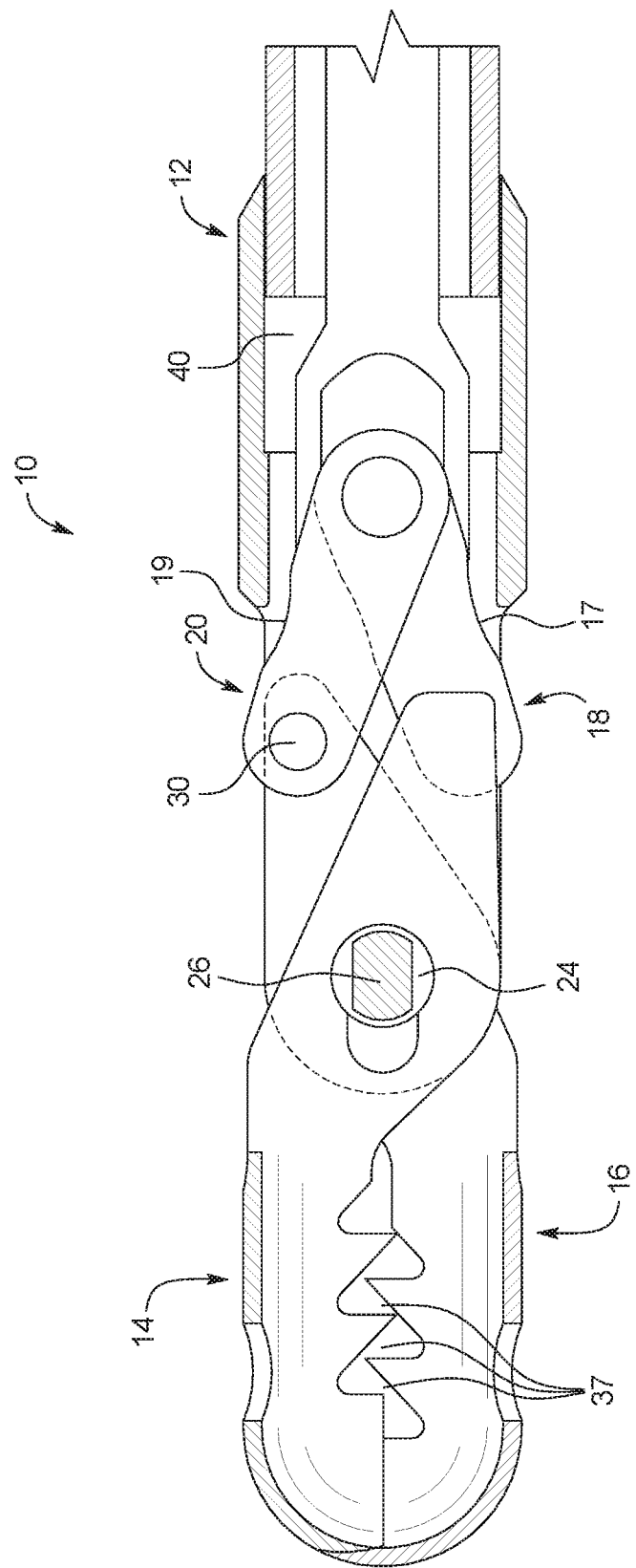
FIG. 3 is a sectional side view of a forceps design.

FIG. 3 shows the structure of the forceps 10 within the housing 12. As can be seen, one of the ends of each the first and second links 18, 20 are pivotably connected to the driver 40. The driver 40 may be a stiff elongated wire or shaft that ideally extends to a point external the patient during the procedure. In some embodiments, the housing 12 may include an elongated shaft with a hollow portion through which the driver 40 is movably disposed. A portion of the housing 12, or another shaft operably connected to the housing 12, ideally extends to a point external the patient during operation. The connecting pin 26 and openings 24, 25 may be designed to allow two degrees of freedom of each of the jaws 14, 16: longitudinal movement along a longitudinal axis of the housing 12 and rotational movement about the connecting pin 26. In this example, the connecting pin 26 has a cross-section that is elongated in shape with two flattened edges and two curved edges. The openings 24, 25 may each include two portions that control the operation of the forceps as described in more detail below. The first opening 24 may include a first cylindrical portion 32 and a first elongated portion 34 (shown in FIGS. 4 and 5). The second opening 25 includes similar portions, a second cylindrical portion 33 and a second elongated portion 35 (not shown). Other shapes for the two portions may also be used. When the connecting pin 26 is partially or fully disposed within the cylindrical portions 32, 33 of the openings 24, 25, the jaws 14, 16 may rotate open and closed. Relatedly, when the jaws 14, 16 are partially or fully closed, the connecting pin 26 may partially or fully mate with the elongated portion 34, 35 of the openings 24, 25 and the jaws 14, 16 may slide longitudinally along the connecting pin 26 via the openings 24, 25 between the positions shown in FIGS. 3 and 8. Once the connecting pin 26 is at least partially disposed within the elongated portions 34, 35 of the openings 24, 25, the elongated shape of the connecting pin 26 may limit full rotational movement of the jaws 14, 16.

Figure 4:
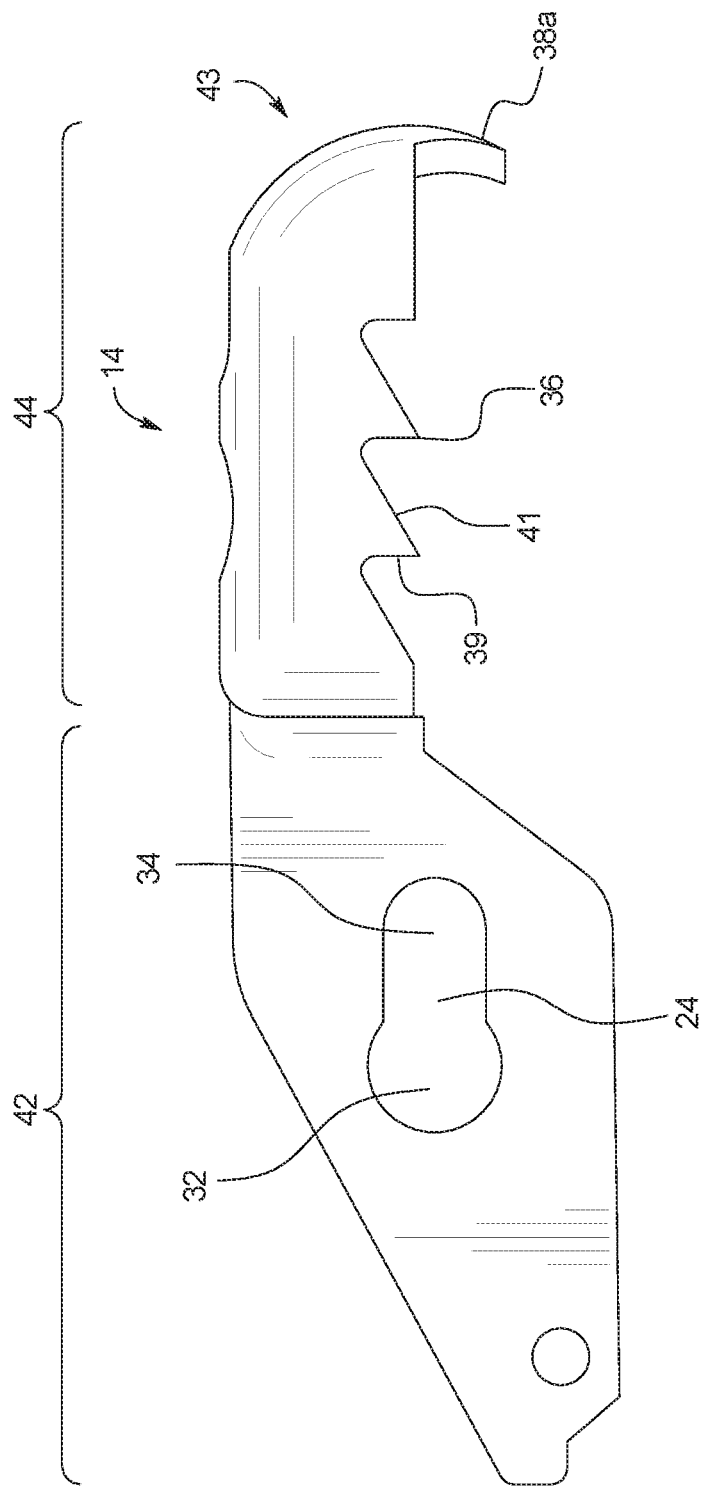
FIG. 4 is a detailed side view of a jaw used in a forceps design.
Figure 5:
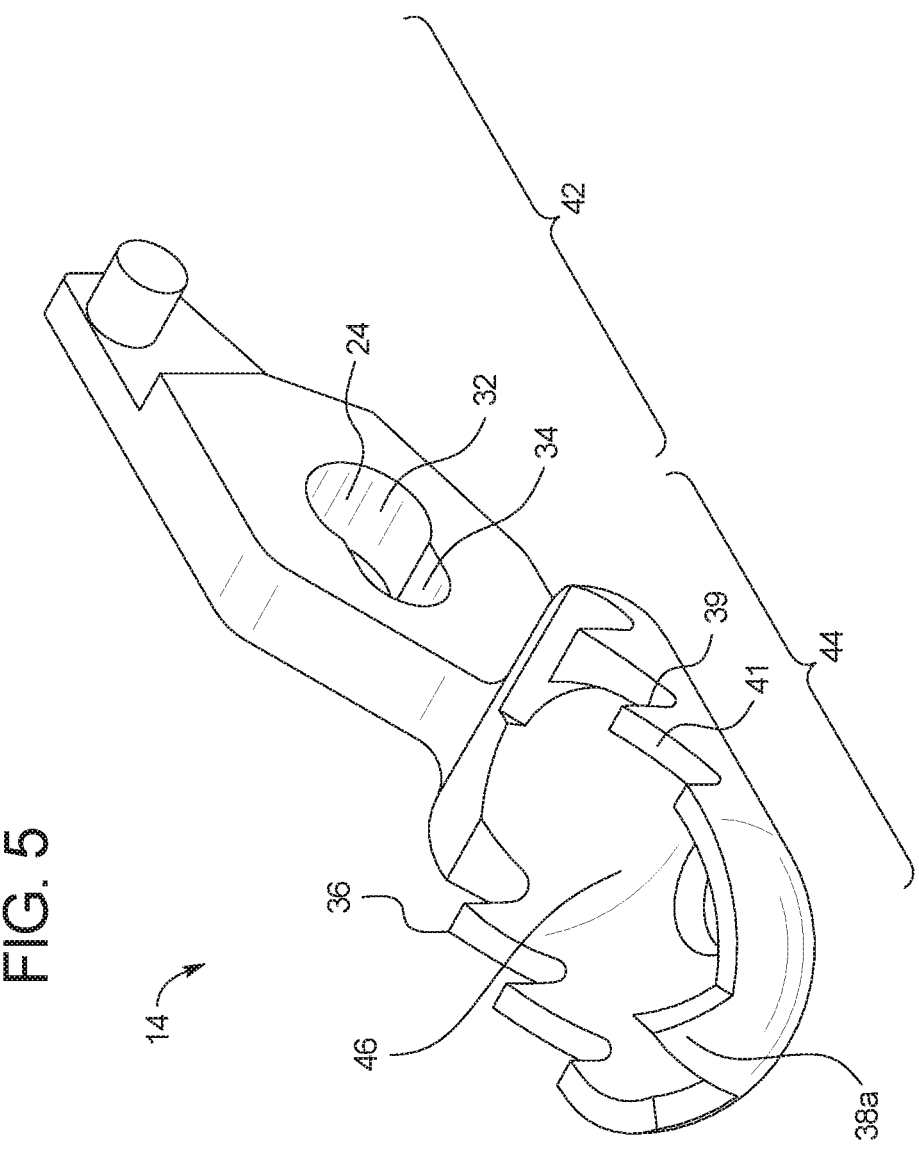
FIG. 5 is a detailed orthographic view of a jaw used in a forceps design.

FIGS. 4 and 5 show detailed views of the first jaw 14, which in some embodiments is identical in design to the second jaw 16. FIG. 5 shows the embodiment of the first jaw 14 that is shown in FIGS. 1-3, while FIG. 4 is an alternate design that may be used in the forceps embodiment discussed in FIGS. 12 and 13 below. The first jaw 14 may include a connection portion 42 and a clamping portion 44. The connection portion 42 interacts with the rest of the forceps 10 as previously described, while the clamping portion 44 is used to interact with tissue or other materials. The clamping portion 44 may be optimized for tissue biopsy collection by having a cup shape design with a hollow portion 46 in the middle of the clamping portion 44. Thus, when the first and second jaws 14, 16 close, the hollow portions 46 provide an open space for tissue to be collected and stored for retrieval. The clamping portion 44 may further include rows of teeth 36. In some embodiments, the teeth 36 may be located on either side of the hollow portion 46. During a biopsy, the tissue sample is most commonly excised from the surrounding tissue by proximally retracting the forceps 10 in the closed configuration while the teeth 36 tear the tissue. To increase the effectiveness of the tissue tearing, teeth 36 may each have a proximal face 39 that extends vertically from the clamping portion 44 and a distal face 41 that extends at a proximal angle from the clamping portion 44. The vertical proximal face 39 may maintain a grip on the tissue more effectively when retracting the forceps 10 and tearing the tissue when compared to an angled face. In other embodiments, the teeth and faces may be arranged differently to achieve various advantages. For example, the proximal face 39 may also extend at a proximal angle from the clamping portion 44 to more effectively grasp the tissue. Both proximal and distal faces 39, 41 may also extend at a distal angle or at other various angles from the clamping portion 44 as desired. Additionally, the jaws 14, 16 may be designed to mate such that the teeth 36 are staggered and gaps 37 exist between the teeth 36 of the two jaws when the jaws 14, 16 mate in the closed configuration (shown in FIG. 3). In one example, the point of a tooth 36 on one of the jaws 14, 16 may mate at the midpoint of the distal face 41 of a tooth 36 on the other jaw 14, 16. This pattern may be repeated for the rest of the teeth 36, thereby forming the aforementioned gaps 37. These gaps 37 provide additional space for the tissue sample to be stored so a sufficient sample size is obtained during the biopsy. The clamping portion 44 may also include a sharptooth, or "rat's tooth" 38a at a distal end 43 of the first jaw 14 with a mating tooth 38b on the second jaw 16 (shown in FIG. 2). The rat's tooth 38a, 38b is effective in providing the initial tearing of the tissue sample. The clamping portion 44 may optionally include a spike 76 disposed within the center of the hollow portion 44 to help secure the tissue within the forceps 10 for removal of the tissue biopsy from the patient (shown as exemplary in FIG. 12). The spike 76 may be formed with the tip pointed distally, which may help anchor the forceps 10 into the tissue and increase the amount of tissue initially grabbed by the forceps 10. The spike 76 may alternatively be formed with the tip pointed vertically or even proximally, which may assist the forceps 10 in maintaining the grip on the tissue during the excising and removal of the sample. While this example describes the design of the clamping portion 44 as optimized for a tissue biopsy, the clamping portion 44 may be altered for various other uses.

Figure 6:
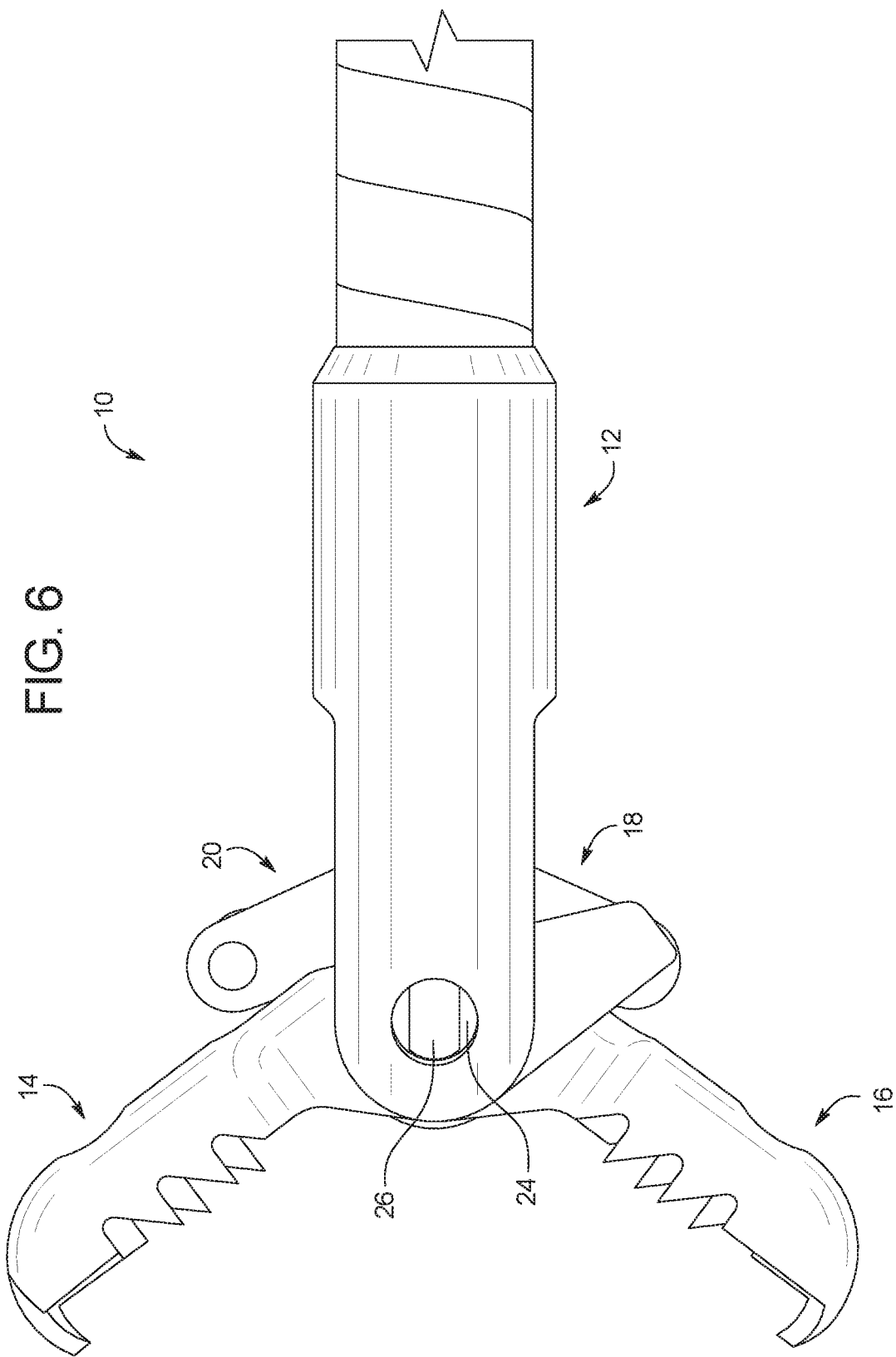
FIG. 6 is a side view of a forceps design in an open configuration.
Figure 7:
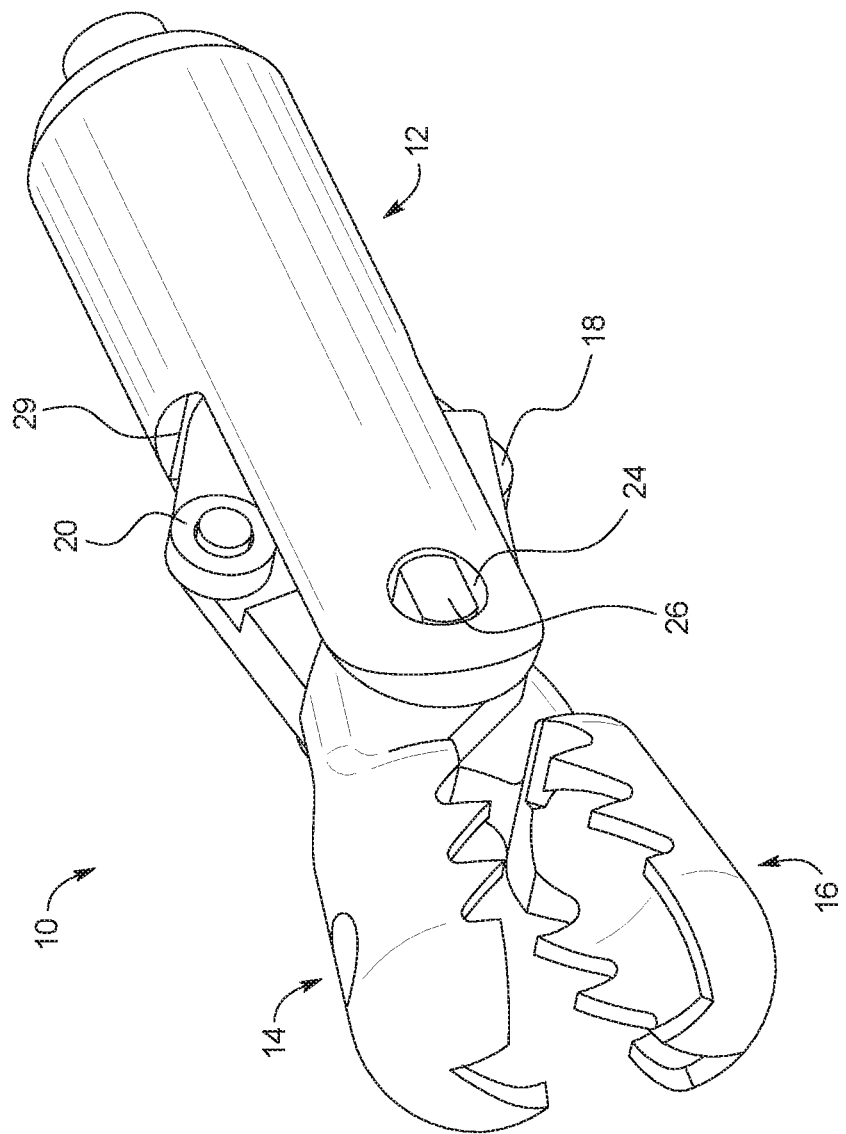
FIG. 7 is a side view of a forceps design during the camming action of the closure cycle.
Figure 8:
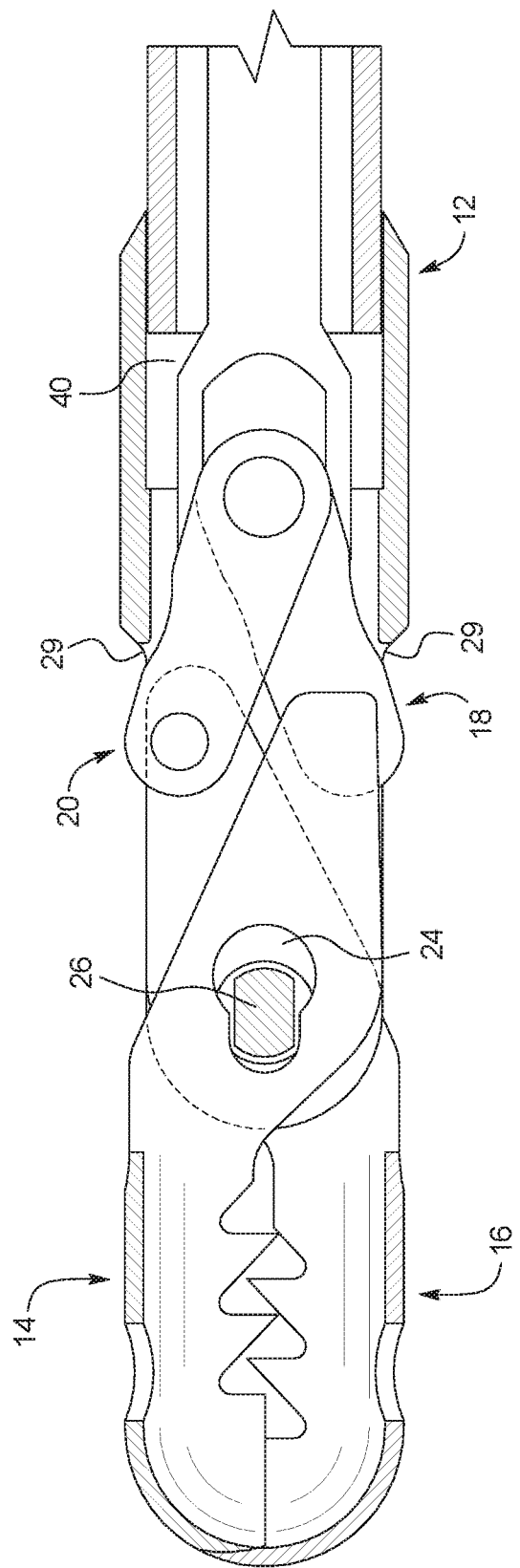
FIG. 8 is a side view of a forceps design in a closed configuration.

FIGS. 6-8 show the forceps 10 in various stages of operation. As described above, the jaws 14, 16 of the forceps 10 may be moved in two separate degrees of freedom: rotationally and longitudinally. Specifically, the jaws 14, 16 may rotate open and closed and also slide longitudinally along a longitudinal axis of the forceps 10. However, in this embodiment, the rotational and longitudinal movement of the jaws 14, 16 does not always occur in discrete and separate stages of operation. Instead, due to the shape of the connecting pin 26 and openings 24, 25 along with the actuating force of the driver 40 and the design of the links 18, 20 and the housing 12, the jaws 14, 16 open and close via a blended motion where the rotational and longitudinal movements of the jaws 14, 16 occur simultaneously during certain stages of the closure cycle. FIG. 6 shows the forceps 10 in an open configuration where the jaws 14, 16 are fully open. In the open configuration, the connecting pin 26 may be fully disposed within the cylindrical portions 32, 33 of the openings 24, 25. To move the jaws 14, 16 to the closed configuration, the driver 40 is moved proximally with respect to the housing 12. As the driver 40 is moved proximally, the ends of the links 18, 20 connected to the driver 40 are correspondingly pulled in a proximal direction, while the ends of the links 18, 20 connected to the jaws 14, 16 are pulled in a proximal direction while also being rotated towards each other. As the links 18, 20 move proximally while also partly rotating towards each other, the jaws 14, 16 each pivot about the connecting pin 26, which causes the jaws 14, 16 to begin to close. Once the jaws 14, 16 pivot about the connecting pin 26 a sufficient amount, the connecting pin 26 may begin to mate with the elongated portions 34, 35 of the openings 24, 25. Thus, the jaws 14, 16 may begin to slide proximally via the connecting pin 26 along the elongated portions 34, 35 of the openings 24, 25 as the jaws 14, 16 continue to rotate closed. As the driver 40 continues to move in a proximal direction, the links 18 and 20 eventually contact the housing 12 at contact points 29 as shown in FIGS. 7 and 8. Once the links 18, 20 contact the housing 12, they may remain in contact as the forceps 10 continue to be moved to the closed configuration. The connecting pin 26 and openings 24, 25 may be designed such that a small amount of clearance exists between the connecting pin 26 and openings 24, 25. While a tight tolerance may be desirable to ensure smooth operation of the forceps 10, providing clearance between the connecting pin 26 and openings 24, 25 may also be advantageous and helps enable blended motion. As the links 18, 20 first contact the housing 12, the initial force provided by the housing 12 against the links 18, 20 causes the links 18, 20 to push back against the jaws 14, 16. The initial force from the housing 12 against the links 18, 20 causes the jaws 14, 16 to slide slightly distally back towards the cylindrical portions 32, 33 of the openings 24, 25. Providing this clearance prevents the connecting pin 26 from binding or catching on the openings 24, 25—thereby ensuring smooth operation of the forceps 10 throughout the closure cycle. Further, the cutout portions 17, 19 in the links 18, 20 provide additional clearance between the links 18, 20 and the housing 12 to limit the likelihood of the forceps 10 binding or catching.

Figure 9:
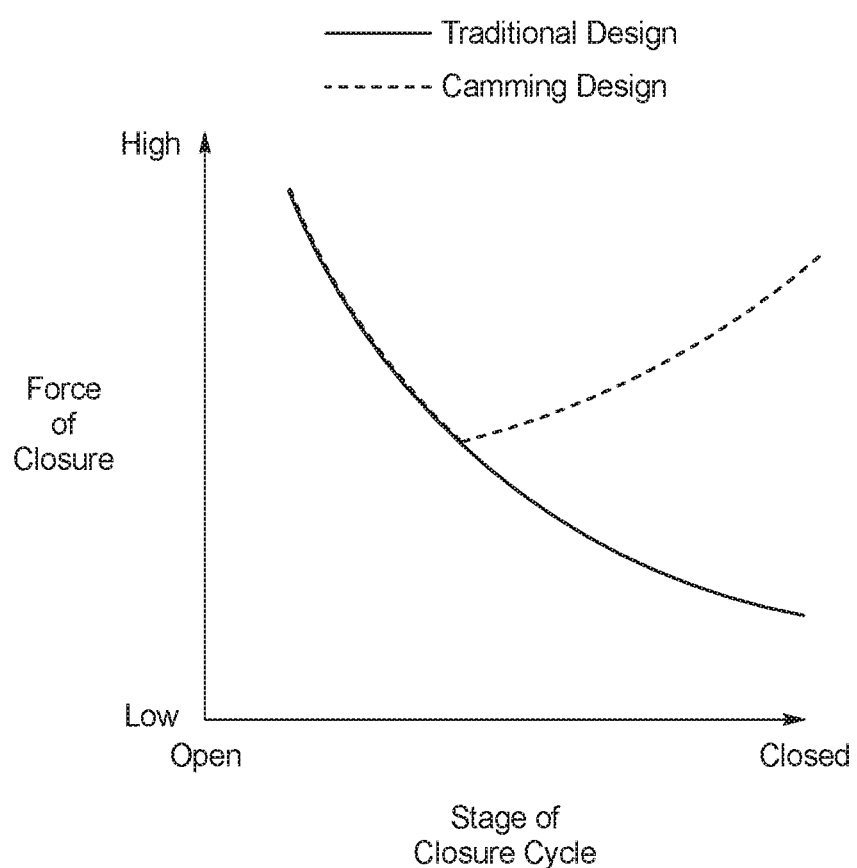
FIG. 9 is a schematic force/closure cycle graph comparing a traditional forceps design and the improved design contemplated herein.

Additionally, a camming action occurs when contact is made between the housing 12 and the links 18, 20. This camming action gives the present design a mechanical advantage over traditional forceps. As discussed previously, traditional linked forceps that utilize a simple scissor-like closing motion do not have a high closing force near the end of the closing motion. FIG. 9 shows a schematic force/closure graph comparing a traditional forceps design (solid line) with the present invention (dotted line). As can be seen for traditional forceps, the closing force is high near the beginning of the closure cycle; however, the closing force continuously decreases as the jaws close. The closing force is at its lowest when the forceps are in the closed configuration. In comparison, while the first portion of the force/closure graph is similar for the present invention, the closure force begins to increase rather than decrease near the latter stages of the closure cycle. This difference in closure force is due, in part, to the aforementioned camming action. The camming action creates a force by the housing 12 against the links 18, 20 which provides a corresponding increasing force against the jaws 14, 16 that urges the jaws 14, 16 towards the closed configuration. Additionally, the aforementioned clearance between the connecting pin 26 and the openings 24, 25 along with the cutout portions 17, 19 of the links 18, 20 may help the camming action occur more smoothly. Without these clearances, the forceps 10 may bind and be inoperable. It is important to note that FIG. 9 is exemplary, and the present embodiment may not necessarily cause the closing force to increase during the latter portion of the closure cycle. Rather, the camming action may instead cause a slight departure from the traditional forceps design's force/closure graph. For example, the closing force may still continue to decrease during the latter stages of the present embodiment's closure cycle, but may decrease less significantly when compared to the traditional forceps closing force. Overall, the present embodiment provides a greater closing force near the latter stages of the closure cycle when compared to a traditional forceps design, and the significance of the departure from the traditional forceps design may vary based on various design characteristics of the present embodiment.

After contact is made between the links 18, 20 and the housing 12, further proximal movement of the driver causes the jaws 14, 16 to continue to close as the aforementioned camming action is maintained. Due to the designed clearance between the openings 24, 25 and the connecting pin 26, the jaws 14, 16, which had previously slid distally due to the initial contact between the housing 12 and the links 18, 20, will once again begin to slide proximally along the longitudinal axis as the connecting pin 26 slides further within the elongated portions 34, 35 of the openings 24, 25. The jaws 14, 16 will continue to rotate together and slide proximally as the driver 40 is further moved in a proximal direction. Eventually, but not necessarily, the jaws 14, 16 are rotated together such that the clamping portions 44 are in contact with one another just prior to the point when the connecting pin 26 contacts the proximal end of the elongated portions 34, 35 of the openings 24, 25. Then, the driver 40 is pulled slightly further proximally until the connecting pin 26 contacts the proximal end of the elongated portions 34, 35 of the openings 24, 25. At this point the forceps 10 are in the closed configuration and the driver 40 may not be moved any further in the proximal direction (FIG. 8). Additionally, as the jaws 14, 16 slide proximally along the elongated portions 34, 35 of the openings 24, 25, the links 18, 20 continue to contact the housing 12, with an increasing force being provided by the housing 12 against the links 18, 20.

Once the forceps 10 are in the closed configuration, the links 18, 20 are at least partially wedged within the housing 12. The wedging of the links 18, 20 and the aforementioned camming action locks the jaws 14, 16 closed and prevents the jaws 14, 16 from being easily or accidentally reopened and thus potentially losing their grip on the object being grabbed. The jaws 14, 16 may also be further prevented from being accidentally reopened by the shape of the connecting pin 26 with respect to the elongated portions 34, 35 of the openings 24, 25, which limits rotational motion of the jaws 14, 16. To move the forceps 10 back to the open configuration, the driver 40 is moved distally relative to the housing 12, thus reversing the closure cycle previously described. The forceps 10 may be moved repeatedly between the open and closed configurations.

Figure 10:
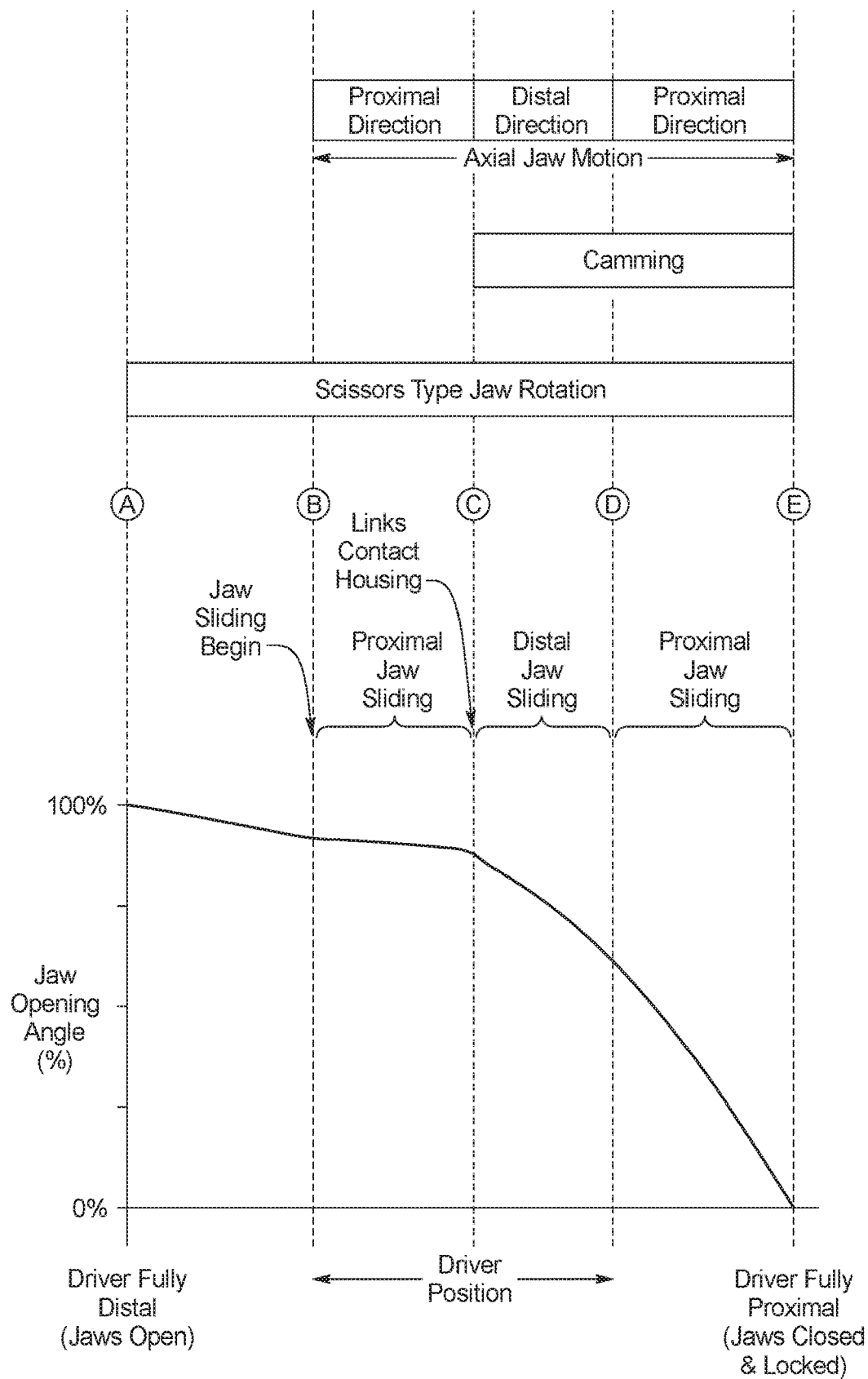
FIG. 10 is a graphical representation of the stages in the closure cycle of a forceps design.

FIG. 10 shows a graphical representation of one embodiment of the closure cycle. As the forceps 10 move from the open configuration to the closed configuration, several changes in the mechanics of the forceps 10 occur. In FIG. 10, the forceps 10 start in the open configuration (A) on the left-hand side of the graph and end in the closed, or locked, configuration (E) on the right-hand side of the graph. First, as the forceps begin to move from the open configuration to the closed configuration, scissors-type rotation of the jaws 14, 16 occur as the jaws 14, 16 rotate about the connecting pin 26 (between A and E). Due to the clearance between the connecting pin 26 and the openings 24, 25, proximal sliding of the jaws 14, 16 will eventually occur while the jaws 14, 16 continue to rotate closed (between B and C). As the jaws 14, 16 are further rotated closed, the links 18, 20 eventually contact the housing 12 (C). At this point the camming action begins (between C and E) and the jaws 14, 16 slide slightly distally due to kinematics and the camming action along with the initial force provided by the housing 12 against the links 18, 20 (between C and D). Eventually, the jaws 14, 16 begin to slide proximally again as the camming action continues and the jaws 14, 16 continue to rotate to a closed configuration (between D and E). Ideally, but not necessarily, the jaws 14, 16 close completely and the scissors-type rotation will cease just prior to the openings 24, 25 limiting proximal motion of the jaws 14, 16. At this point, the forceps 10 are in the closed, and fully locked, configuration (E). This is merely one potential embodiment of a closure cycle. The forceps 10 may be altered such that the rotation, sliding, and contact with the housing may occur at various points during the closure cycle as desired.

In the present embodiment, the links 18, 20 are designed to initially contact the housing 12 near the midpoint of the closure cycle. Beginning the camming action mid-stroke is advantageous as additional closure force is needed near that point in the closure cycle. Starting the camming action too early in the closure cycle puts unnecessary stress on the links 18, 20 and the housing 12, while starting the camming action too late eliminates the advantages provided by the camming action. However, the forceps 10 can be designed to start the camming action earlier or later as desired. For example, the links 18, 20 can be redesigned or the forked portion 22 in the housing 12 can be made shorter, longer, or otherwise shaped differently. Further, the shape of the links 18, 20 may be altered, such as the depth or position of the cutout portions 17, 19.

In the present embodiment, the openings 24, 25 are formed within the jaws 14, 16 and the connecting pin 26 is fixedly attached to the housing 12. In an alternative embodiment, one opening 24 may be formed on one fork of the forked portion 22 of the housing 12 while the other opening 25 is formed on the other fork of the forked portion 22. The forceps may then also include a first connecting pin fixedly attached to the first jaw 14 and pivotably and slidably received within the first opening 24 and a second connecting pin fixedly attached to the second jaw 16 and pivotably and slidably received within the second opening 25.

The connecting pin 26 may have various shapes while the openings 24, 25 may be altered to provide various kinematic advantages. For example, the connecting pin 26 may be ovular in shape, which may allow the forceps 10 and jaws 14, 16 to smoothly transition from rotating about the connecting pin 26 within the cylindrical portions 32, 33 of the openings 24, 25 to sliding longitudinally along the elongated portions 34, 35 of the openings 24, 25. Alternatively or additionally, the openings 24, 25 may be curved or have a teardrop shape. The clearance between the connecting pin 26 and openings 24, 25 may allow the jaws 14, 16, by way of the openings 24, 25, to slide smoothly along the connecting pin 26 as the forceps 10 are moved from the open configuration to the closed configuration.

Figure 11:
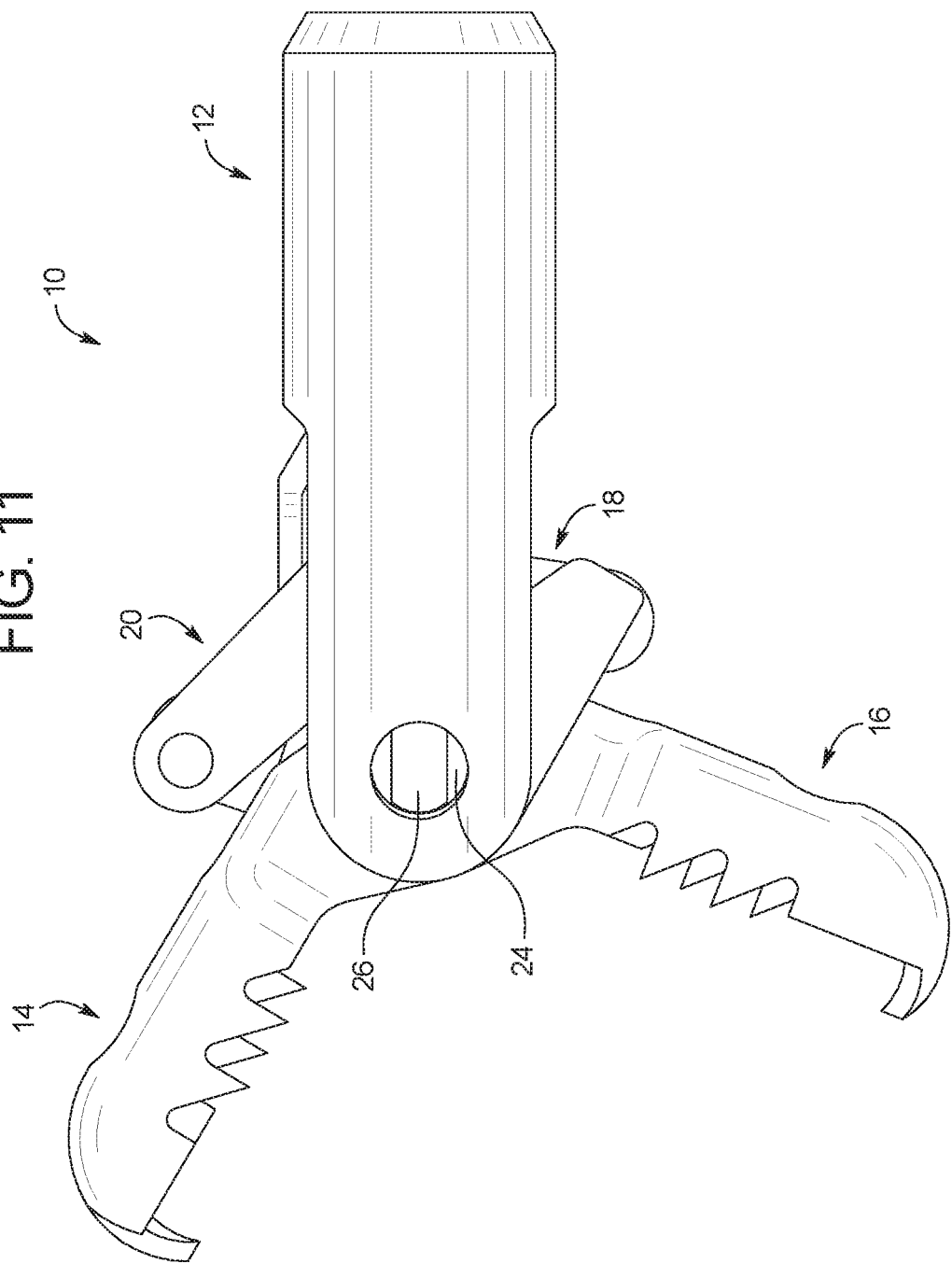
FIG. 11 is a side view of a forceps design with an additional degree of freedom.

The forceps 10 may also be designed with an additional degree of freedom when in the open configuration. In FIG. 11, the forceps 10 are shown with the jaws 14, 16 rotated in the same direction around the connecting pin 26 such that the jaws remain in the open configuration during this rotation. The jaws 14, 16 can be rotated together side to side while the jaws 14, 16 are maintained in the open configuration. This freedom of movement is achieved by maintaining a clearance between the internal passageway of the housing 12 and the driver 40. Thus, when the jaws 14, 16 come into contact with a body structure, the force between the body structure and the jaws 14, 16 may cause the jaws 14, 16 to rotate around the connecting pin 26 such that the clamping portions 44 of the jaws 14, 16 align with the target tissue. This freedom of movement may be advantageous to allow the forceps 10 to navigate to difficult areas of tissue in tight body lumens or through the passageways of an introducer device.

The forceps 10 may optionally include the ability to electrify the jaws 14, 16. When the jaws 14, 16 are grasping the tissue, an electric current may be run through the jaws 14, 16 to cauterize the tissue, which may help in separating a tissue sample from the surrounding tissue and to prevent bleeding.

The forceps 10 may be made with any metal that can be machined or formed into the components required to make the forceps assembly including, but not limited to: stainless steel, titanium, cobalt chromium, and nickel cobalt. Additive manufacturing may also be used to manufacture the forceps. Additionally, the forceps 10 may be made with any polymer, ideally a biocompatible one including, but not limited to: injection molded plastic or a reinforced polymer composite. Additionally, any combination of metal and plastic may be used to make the forceps such as a metal with an overmolded plastic.

While this embodiment is described in terms of open and closed configurations, the forceps 10 may have additional distinct stages or configurations throughout the closure cycle. For example, rather than the smooth and continuous, or blended, motion described above that includes rotational and longitudinal movement of the jaws 14, 16 along with a camming action, there may be distinct stages of the closure cycle where only rotational motion of the jaws 14,16 occurs, followed by a second distinct stage where only longitudinal motion of the jaws 14, 16 occurs. Alternatively, additional configurations may be contemplated, such as providing a fourth configuration that may allow various kinematic advantages or an increased closing force.

The forceps 10 previously described may be used in a tissue biopsy procedure. A scope, often an endoscope, may be advanced into a patient's body lumen, with the camera used to locate the target site. The forceps 10 may then be advanced to the target site through a lumen of the scope or along the external surface of the scope. The forceps 10 are ideally advanced in the closed configuration due to the smaller profile of the forceps 10 when compared to the open configuration. Once the jaws 14, 16 are positioned near the tissue to be biopsied, the forceps 10 are moved to the open configuration by moving the driver 40 distally with respect to the housing 12. Once the forceps 10 are in the open configuration, the jaws 14, 16 are positioned adjacent to the tissue and then moved to the closed configuration such that the jaws 14, 16 close around a portion of the tissue. The forceps 10 are next retracted proximally to tear a tissue sample from the surrounding tissue. Since the forceps 10 are automatically locked by the camming action and the connecting pin 26 and the closing force is high, the jaws 14, 16 may strongly grasp the tissue, thus maximizing the amount of tissue excised from the surrounding tissue. Next, the forceps 10, along with the tissue sample, are removed from the patient's body lumen and endoscope. The scope may then be removed as well. Alternatively, the scope and forceps 10 may be removed together. Also alternatively, the forceps 10 may be inserted without the use of a scope or through a catheter. The forceps 10 may also be positioned at the tissue sampling site with the use of other well-known imaging methods such as fluoroscopy.

Figure 12:
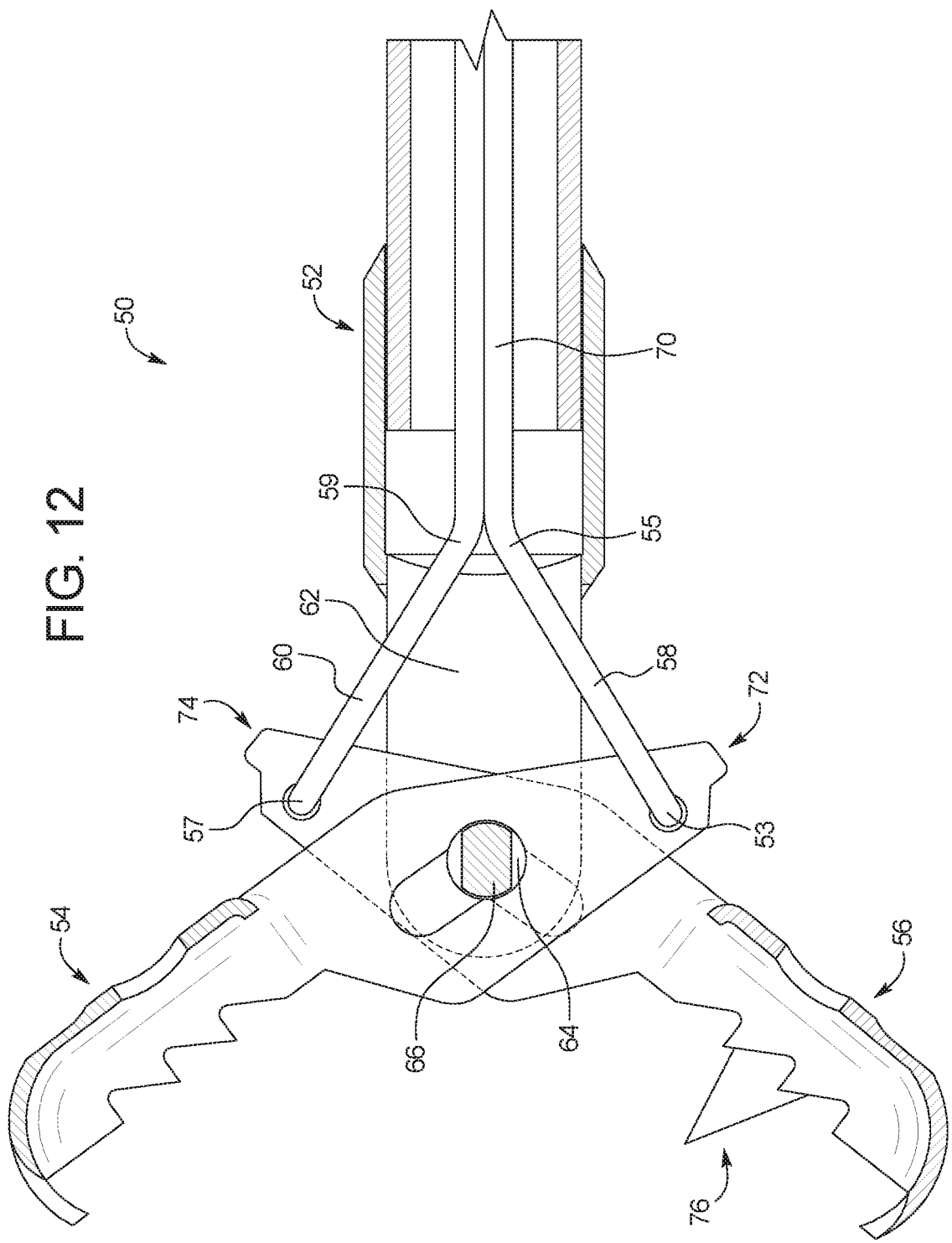
FIG. 12 is a sectional side view of another forceps design in an open configuration.
Figure 13:
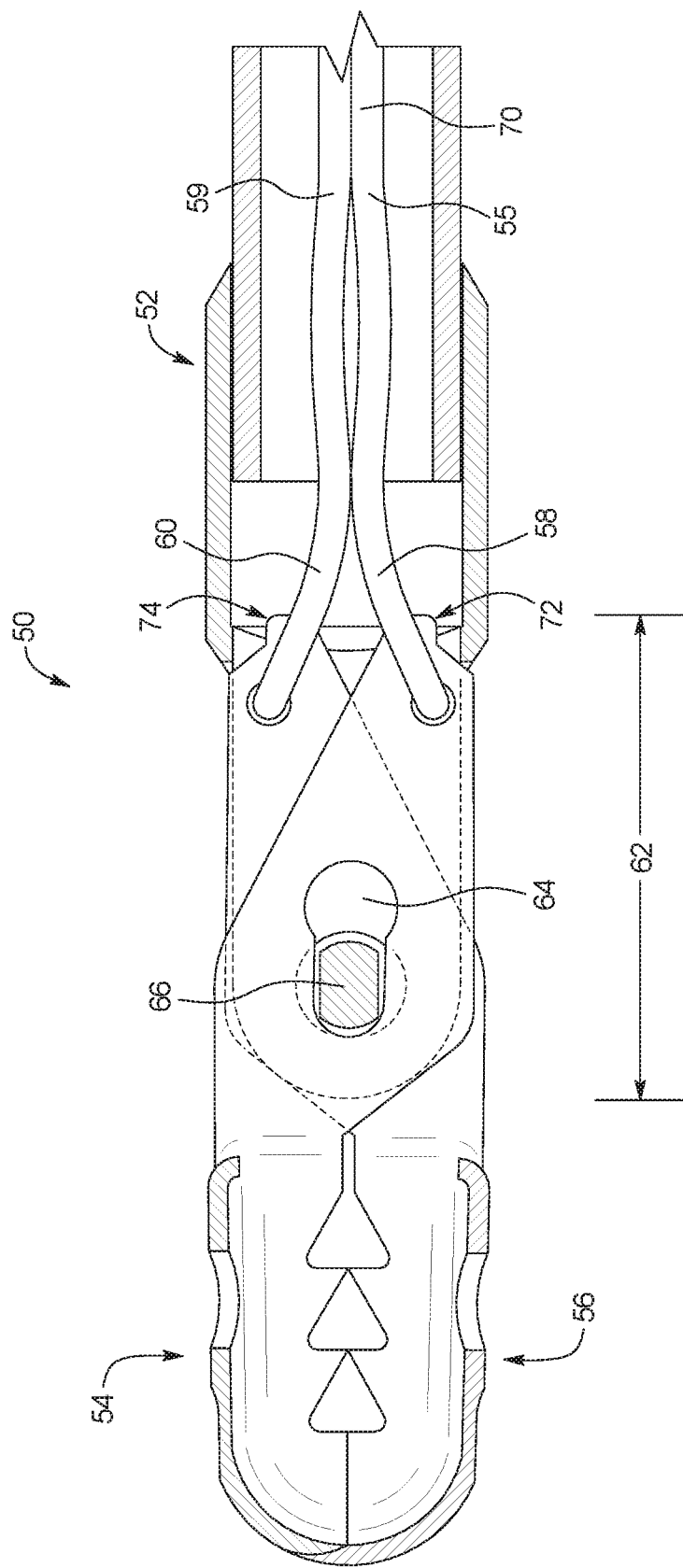
FIG. 13 is a sectional side view of another forceps design in a closed configuration.

In another embodiment of the invention a forceps 50 is provided. FIG. 12 shows the forceps 50 in an open configuration while FIG. 13 shows the forceps 50 in a closed, or locked, configuration. The forceps 50 may include a housing 52, a first jaw 54, and a second jaw 56. The forceps 50 may further include a first connection member 58 and a second connection member 60. The distal end of the housing 52 may include a forked portion 62. The first jaw 54 may include a first opening 64 and the second jaw 56 may include a second opening 65 (concentric with the first opening 64 when viewed from the side angle in FIG. 13). The first and second jaws 54, 56 may be pivotably connected to the forked portion 62 of the housing 52 by a connecting pin 66 threaded through the first and second openings 64, 65. The connecting pin 66 may be fixedly attached to the forked portion 62 of the housing 52. The first jaw 54 may be pivotably connected to one end 53 of the first connection member 58. The other end 55 of the first connection member 58 may be operably connected to a driver 70. The second jaw 56 may be pivotably connected to one end 57 of the second connection member 60. The other end 59 of the second connection member 60 may be operably connected to the driver 70. In this embodiment the first and second connection members 58, 60 extend proximally to a point to where they meet adjacent to one another. The connection members 58, 60 then extend further proximally together to form the driver 70, which ideally extends to a point external the patient during the procedure. However, the driver 70 may also have a variety of other designs, including a stiff elongated wire or shaft. The housing 52 is ideally an elongated shaft with a hollow portion through which the driver 70 is movably disposed. A portion of the housing 52, or another shaft operably connected to the housing 52, may extend to a point external the patient during operation. As with the previous embodiment, the connecting pin 66 and openings 64, 65 may be designed to allow two degrees of freedom: longitudinal and rotational movement of the jaws 14, 16.

Similar to the operation of the previously discussed embodiment, the forceps 50 may be repeatedly moved between the open configuration and closed configuration by longitudinally moving the driver 70 relative to the housing 52. To move the forceps 50 from the open configuration to the closed configuration, the driver 70 is moved proximally relative to the housing 52. As the driver 70 is moved proximally, the driver 70 pulls the first and second connection members 58, 60 proximally as well. As the first and second connection members 58, 60 move proximally, the jaws 54, 56 pivot about the connecting pin 66, which causes the jaws 54, 56 to begin to close. Eventually, further proximal movement of the driver 70 will cause the jaws 54, 56, and the openings 64, 65 in the jaws 54, 56, to slide longitudinally in a proximal direction with respect to the connecting pin 66. Finally, and possibly simultaneously, the jaws 54, 56 will slide proximally to a point where the connecting pin 66 is secured within the elongated portion of the openings 64, 65 and the jaws 54, 56 are rotated together such that the jaws 54, 56 are in contact with one another, thus reaching the closed configuration. When in the closed configuration as shown in FIG. 14, the forceps 50 may be further secured by designing the proximal ends of the jaws 54, 56 such that a portion of them are disposed within the housing 52 while the forceps 50 are in the closed configuration. Ideally, the jaws 54, 56 each have respective notches, or protrusions, 72, 74. When the connecting pin 66 is fully or partially within the cylindrical portion of the opening 64, the notches 72, 74 are outside of the housing 52, thus allowing free rotation of the jaws 54, 56 without interference from the housing 52. Once the connecting pin 66 and the jaws 54, 56 are pulled further proximally such that the connecting pin 66 is fully or partially within the elongated portion of the opening 64, the notches 72, 74 are pulled within the housing 52. Therefore, when in the closed configuration, the inner surface of the housing 52 contacts the notches 72, 74, thus limiting free rotation of the jaws 54, 56 and thereby locking them closed.

Additionally, the shape of the connecting pin 66 with respect to the elongated portion of the openings 64, 65 may limit rotational motion of the jaws 54, 56. Thus, the jaws 54, 56 are locked and unable to rotate substantially about the connecting pin 66 to the open configuration, thereby preventing or eliminating accidental release of the tissue or other item the forceps are grabbing. To move the forceps 50 back to the open configuration, the driver 70 is moved distally relative to the housing 52, reversing the closure cycle previously described.

The forceps 50 may be used in a tissue biopsy procedure in a similar manner as described with previous embodiments. The forceps 50 are moved within a body lumen to where a tissue sample is to be collected. The forceps are then moved from the open configuration to the closed configuration such that the jaws 54, 56 are closed around a piece of tissue and the forceps 50 are automatically locked shut by the mechanisms described above. While maintaining the forceps 50 in the closed configuration, the forceps 50 are pulled proximally, thus tearing the tissue sample from the surrounding tissue. The forceps 50, along with the collected tissue sample, are then removed from the patient.

The forceps 50 may be modified in various ways as described in previous embodiments including, but not limited to, modifying the shape of the jaws 54, 56 to suit various functions.

While in these embodiments the forceps are shown and described as biopsy forceps, the shape and structure of the forceps may take many forms and serve many purposes and functions, all in accordance with the teachings of the present invention. This includes the use of the forceps locking/camming design in a non-medical context.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A forceps comprising:
    a housing defining an internal passageway and a longitudinal axis extending between proximal and distal ends of the housing;
    a first jaw slidably and pivotably connected to the housing, where the first jaw comprises a first opening including a first substantially cylindrical portion and a first substantially elongated portion; a second jaw slidably and pivotably connected to the housing where the second jaw comprises a second opening including a second substantially cylindrical portion and a second substantially elongated portion;
    a first connection member having a first end pivotably connected to the first jaw;
    a second connection member having a first end pivotably connected to the second jaw;
    a connecting pin that slidably and pivotably connects the first and second jaws to the housing; and
    a driver operably connected to a second end of the first connection member and a second end of the second connection member; wherein the first and second jaws further comprise an open configuration and a closed configuration,
    wherein longitudinal movement of the driver in a proximal direction relative to the housing rotates the first and second jaws with respect to the connecting pin when the connecting pin is disposed within the first and second substantially cylindrical portions of the first and second openings relative to the housing from the open configuration towards the closed configuration,
    wherein longitudinal movement of the driver in the proximal direction also moves the first and second jaws longitudinally with respect to the connecting pin along the first and second substantially elongated portions of the first and second openings, along the longitudinal axis of the housing from the open configuration towards the closed configuration,
    wherein the first and second jaws are not fully rotatable between the open configuration and the closed configuration when the connecting pin is at least partially disposed within the first and second substantially elongated portions; and
    wherein during at least a portion of the movement of the first and second jaws from the open configuration to the closed configuration, at least one of the first and second connection members contacts the housing to urge the first and second jaws towards the closed configuration.

2. The forceps of claim 1, wherein: the first connection member comprises a first link; and the second connection member comprises a second link.

3. The forceps of claim 1, wherein: longitudinal movement of the driver in a distal direction moves the first and second jaws longitudinally along the longitudinal axis of the housing from the closed configuration towards the open configuration, wherein movement of the driver in the distal direction also rotates the first and second jaws relative to the housing from the closed configuration towards the open configuration.

4. The forceps of claim 1, wherein: in the closed configuration at least a portion of at least one of the first and second connection members is wedged against the housing.

5. The forceps of claim 1, wherein: in the closed configuration at least a portion of at least one of the first and second connection members is wedged against the housing.

6. The forceps of claim 5, wherein: the first jaw further comprises a first clamping portion and the second jaw further comprise a second clamping portion; and in the closed configuration the first clamping portion and second clamping portion are closer together than when in the open configuration.

7. The forceps of claim 1, wherein: the first jaw further comprises a first clamping portion and the second jaw further comprise a second clamping portion; and in the closed configuration the first clamping portion and second clamping portion are closer together than when in the open configuration.

8. The forceps of claim 1, wherein: when in the open configuration the first and second jaws are rotatable about the connecting pin while the first and second jaws are maintained in the open configuration.

\* \* \* \* \*